(12) United States Patent
LeMay et al.

(10) Patent No.: US 8,444,590 B2
(45) Date of Patent: May 21, 2013

(54) TAPERED TAMPON APPLICATOR WITH PETALS AND TAPER RATIO

(75) Inventors: Jessica E. LeMay, New York, NY (US);
Kathryn G. Bennett, Fairfield, CT (US);
Keith Edgett, Middletown, DE (US);
Dane R. Jackson, New Hanover, PA (US); Rejai Jamshid, Dover, DE (US)

(73) Assignee: Playtex Products, Inc., Westport, CT (US)

( * ) Notice: Subject to any disclaimer, the term of this patent is extended or adjusted under 35 U.S.C. 154(b) by 2553 days.

(21) Appl. No.: 10/601,771

(22) Filed: Jun. 20, 2003

(65) Prior Publication Data

US 2004/0064082 A1    Apr. 1, 2004

Related U.S. Application Data

(60) Provisional application No. 60/390,751, filed on Jun. 21, 2002.

(51) Int. Cl.
*A61F 13/30* (2006.01)
*A61F 13/26* (2006.01)

(52) U.S. Cl.
USPC .................................. 604/14; 604/15; 604/11

(58) Field of Classification Search
USPC ........ 604/368, 11–18, 904; D24/141; 28/118; 424/430
See application file for complete search history.

(56) References Cited

U.S. PATENT DOCUMENTS

| 3,204,635 A | 9/1965 | Voss et al. ..................... 128/263 |
| 3,347,234 A | 10/1967 | Voss .............................. 128/260 |
| 3,358,354 A | 12/1967 | Voss et al. ........................ 29/419 |
| 3,433,225 A | 3/1969 | Voss et al. ..................... 128/263 |
| 3,581,744 A | 6/1971 | Voss et al. ..................... 128/263 |
| 3,628,533 A | 12/1971 | Ioyer ................................ 604/15 |
| 3,674,026 A | 7/1972 | Werner et al. ................. 128/263 |
| 3,764,438 A | 10/1973 | Voss et al. ..................... 156/425 |
| 3,765,416 A * | 10/1973 | Werner et al. ................... 604/18 |
| 3,895,634 A * | 7/1975 | Berger et al. .................... 604/14 |

(Continued)

FOREIGN PATENT DOCUMENTS

| FR | 1515087 | 3/1968 |
| GB | 549053 | 11/1942 |

(Continued)

OTHER PUBLICATIONS

Box Cover—Assure! Natural Fit Tampons.

(Continued)

*Primary Examiner* — Susan Su
(74) *Attorney, Agent, or Firm* — Ohlandt, Greeley, Ruggiero & Perle, L.L.C.

(57) ABSTRACT

There is provided a tampon applicator having a plunger and a barrel with a tapered insertion, which provides enhanced insertion comfort to a user. The taper of the insertion tip is defined by a ratio of the length of the taper projection along a longitudinal axis of the barrel to the length of the taper projection along a radius of the barrel at a base region of the insertion tip. The insertion end of the barrel preferably has two or more petals for enhanced user comfort. Preferably, the petals have a substantially uniform thickness. The barrel may also have a fingergrip for ease of use of the applicator during insertion, expulsion of the pledget, and removal from the vagina.

65 Claims, 6 Drawing Sheets

U.S. PATENT DOCUMENTS

| | | | | |
|---|---|---|---|---|
| 3,934,584 | A | 1/1976 | Corio | 4/59 |
| D250,049 | S | 10/1978 | Hite, Jr. | |
| D250,663 | S | 12/1978 | Koch et al. | 604/15 |
| 4,361,150 | A | 11/1982 | Voss | 128/263 |
| 4,412,833 | A | 11/1983 | Wiegner et al. | 604/14 |
| 4,428,370 | A | 1/1984 | Keely | 4/15 |
| 4,453,925 | A | 6/1984 | Decker | 604/14 |
| 4,479,791 | A | 10/1984 | Sprague | 604/14 |
| 4,536,178 | A | 8/1985 | Lichstein et al. | 604/15 |
| 4,726,805 | A | 2/1988 | Sanders, III | 604/15 |
| 4,846,802 | A | 7/1989 | Sanders, III | 604/15 |
| 4,900,299 | A | 2/1990 | Webb | 4/15 |
| 4,921,474 | A | 5/1990 | Suzuki | 604/15 |
| 5,267,953 | A | 12/1993 | Paul et al. | 604/15 |
| 5,279,541 | A | 1/1994 | Frayman et al. | 604/14 |
| 5,290,501 | A | 3/1994 | Klesius | 264/322 |
| 5,330,421 | A | 7/1994 | Tarr et al. | 604/14 |
| 5,348,534 | A | 9/1994 | Tomaszewski et al. | 604/14 |
| 5,385,542 | A * | 1/1995 | Rawlings | 604/14 |
| 5,389,067 | A | 2/1995 | Rejai | 604/14 |
| 5,437,628 | A | 8/1995 | Fox et al. | 604/14 |
| 5,501,063 | A | 3/1996 | Tews et al. | |
| 5,533,966 | A | 7/1996 | Schoelling | 604/18 |
| 5,569,177 | A | 10/1996 | Fox et al. | 604/15 |
| 5,571,540 | A | 11/1996 | Weyenberg et al. | 425/343 |
| 5,746,710 | A | 5/1998 | Nielsen et al. | 609/14 |
| 5,782,793 | A | 7/1998 | Nielsen et al. | |
| 5,786,793 | A | 7/1998 | Maeda et al. | 343/700 |
| 5,792,096 | A | 8/1998 | Rentmeester et al. | 604/14 |
| 5,827,214 | A | 10/1998 | Fox et al. | 604/14 |
| 5,891,081 | A | 4/1999 | McNelis et al. | 604/14 |
| 5,928,183 | A | 7/1999 | Fox et al. | 604/14 |
| 5,931,803 | A | 8/1999 | Jackson | |
| 6,019,743 | A | 2/2000 | Cole et al. | 604/15 |
| 6,024,716 | A | 2/2000 | Rejai | |
| 6,045,526 | A | 4/2000 | Jackson | 604/15 |
| 6,068,899 | A | 5/2000 | Osborn, III et al. | 428/35.2 |
| 6,179,802 | B1 | 1/2001 | Jackson | 604/15 |
| 6,254,566 | B1 | 7/2001 | Buck et al. | 604/15 |
| 6,270,470 | B1 | 8/2001 | Buck et al. | 604/15 |
| 6,432,075 | B1 | 8/2002 | Wada et al. | 604/15 |
| 6,432,076 | B1 | 8/2002 | Wada et al. | 604/15 |
| 2001/0056253 | A1 * | 12/2001 | Suga | 604/11 |
| 2002/0026140 | A1 | 2/2002 | McNamara | 604/12 |

FOREIGN PATENT DOCUMENTS

| | | |
|---|---|---|
| GB | 1016867 | 1/1966 |
| JP | 58-149756 | 9/1983 |
| JP | H08503151 A | 4/1996 |
| JP | H10513084 A | 12/1998 |
| JP | 2001500046 A | 1/2001 |
| JP | 201145658 A | 5/2001 |

OTHER PUBLICATIONS

Box Cover—Rely—The first tampon made of tiny sponges and super absorbent fibers.
Office Action dated Jan. 4, 2007 for corresponding Canadian Patent Application No. 2,490,244.
European Search Report dated Aug. 16, 2012 for corresponding European Patent Application No. 03737197.8-1217.
Decision of Rejection dated Dec. 9, 2008 for corresponding Japanese Patent Application No. 2004-515978 with English translation.
Notice of Reasons for Rejection dated Jul. 8, 2008 for corresponding Japanese Patent Application No. 2004-515978 with English translation.
Notice of Reasons for Rejection dated Sep. 28, 2010 for corresponding Japanese Patent Application No. 2004-515978 with English translation.
Appeal Decision of Rejection dated Jun. 7, 2011 for corresponding Japanese Patent Application No. 2004-515978 with English summary.
Official Notice of Preliminary Rejection dated Aug. 31, 2006 for corresponding Korean Patent Application No. 2004-7020629 with English translation.
Official Notice of Final Rejection dated Oct. 25, 2007 for corresponding Korean Patent Application No. 10-2004-7020629 with English translation.
Official Notice of Preliminary Rejection dated Apr. 24, 2008 for corresponding Korean Patent Application No. 10-2008-7001937 with English translation.
Official Action dated Dec. 16, 2010 for corresponding Mexican Patent Application No. PA/a/2004/012512 with English translation.
Written Opinion dated Dec. 17, 2004 for corresponding International Patent Application No. PCT/US2003/019420.
International Preliminary Report on Patentability dated Apr. 12, 2005 for corresponding International Patent Application No. PCT/US2003/019420.
International Preliminary Report on Patentability dated Jul. 2, 2008 for corresponding International Patent Application No. PCT/US2003/019420.
Supplementary European Search Report Dated Aug. 1, 2011 From Corresponding EP Application No. 03 73 7197.

* cited by examiner

TAPERED TAMPON APPLICATOR WITH PETALS AND TAPER RATIO

RELATED APPLICATION

This application claims priority from U.S. Provisional Patent Application No. 60/390,751 filed on Jun. 21, 2002, pending.

BACKGROUND OF THE INVENTION

1. Field of the Invention

The present invention relates to an insertion device, such as a catamenial tampon applicator. More particularly, the present invention relates to a tapered tampon applicator. The tapered tampon applicator can be formed from any suitable material, including cardboard.

2. Description of the Prior Art

The majority of commercial tampon applicators are of approximately uniform cross-section and are formed from two components, namely a barrel and a plunger. The barrel has an insertion end that may be blunt and open-ended. In the alternative, the insertion end of the barrel may be rounded or dome-shaped, and may include a number of petals. This arrangement lends itself to greater ease of insertion and insertion comfort to a user, as opposed to the blunt, open-ended design.

Despite the options of petal-tipped applicators commercially available at present, tampon users are generally dissatisfied with the level of comfort provided by these applicators upon insertion. Through both qualitative and quantitative consumer research, it has been determined that providing a tapered insertion tip greatly enhances the actual and perceived level of comfort associated with inserting a tampon applicator.

An applicator barrel with a rounded or dome-shaped end with petals and associated methods of making such applicators is well known in the art of tampons. However, further modification to the applicator insertion end, such as tapering, especially with cardboard applicators, is not prevalent in the art. This is primarily due to a need to modify existing processes or provide new processes for forming tampons with tapered ends. This can be especially difficult with cardboard applicators.

Therefore, there is a need for a tampon applicator, and more particularly a cardboard applicator, that can be manufactured with a tapered, or non-hemispherical portion or portions on the barrel, which imparts enhanced user comfort and ease of use.

SUMMARY OF THE INVENTION

It is an object of the present invention to provide a tampon applicator that has a tapered insertion end.

It is another object of the present invention to provide a tampon applicator that has a tapered main barrel body section and a tapered insertion end.

It is still another object of the present invention to provide a tampon applicator that has a tapered insertion end, wherein the cross-section of the tip is not comprised of any straight sections.

It is yet another object of the present invention to provide such a tapered tampon applicator having an insertion end with two or more petals.

It is a further object of the present invention to provide such a tapered tampon applicator having petals with a uniform or substantially uniform thickness.

It is still a further object of the present invention to provide such a tapered tampon applicator having one or more weakened regions formed at the base region of each petal.

It is yet a further object of the present invention to provide such a tapered tampon applicator with a fingergrip area.

It is another object of the present invention to provide such a tapered tampon applicator that has a barrel formed from cardboard.

These and other objects of the present invention will be appreciated from a tampon applicator having a plunger and a tapered insertion tip, tapered barrel, or both, which provides enhanced insertion comfort to a user. The taper of the barrel is defined by a ratio of the largest radius to the radius of the barrel at the base of the insertion tip. The taper of the insertion tip is defined by the ratio of the length of the taper projection along the vertical axis of the barrel to the projection length along the horizontal axis of the barrel. The insertion end of the barrel preferably has two or more petals for enhanced user comfort. Preferably, each of the petals has a uniform or substantially uniform thickness. The barrel may also include a fingergrip area for ease of use of the applicator during insertion, expulsion of the pledget, and subsequent removal of the applicator from the vagina.

DETAILED DESCRIPTION OF THE INVENTION

Figure 1:
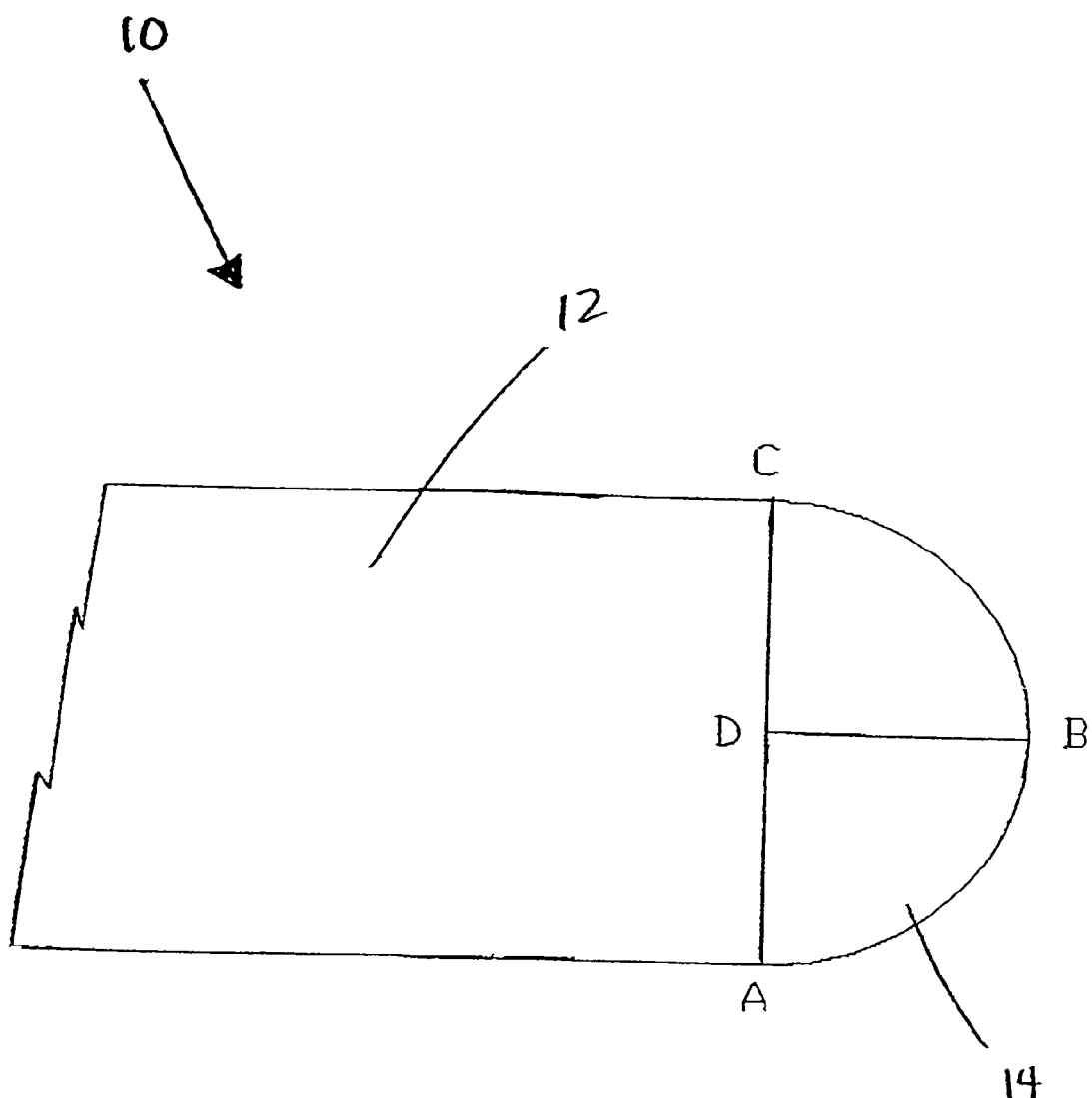
FIG. 1 is a plan view of a prior art tampon applicator with a rounded or dome-shaped insertion end.

Referring to the drawings and, in particular FIG. 1, a typical, prior art commercial tampon applicator is represented generally by reference numeral 10. Applicator 10 has a barrel 12 with a rounded or dome-shaped insertion tip 14. Rounded or dome-shaped insertion end 14 can be defined by a ratio of the length of the rounded curve or dome projection along the horizontal axis, as represented by line BD to the projection length along the vertical axis, as represented by line CD. For the rounded or spherical shape of insertion tip 14, length BD/length CD=1.00.

Figure 2:
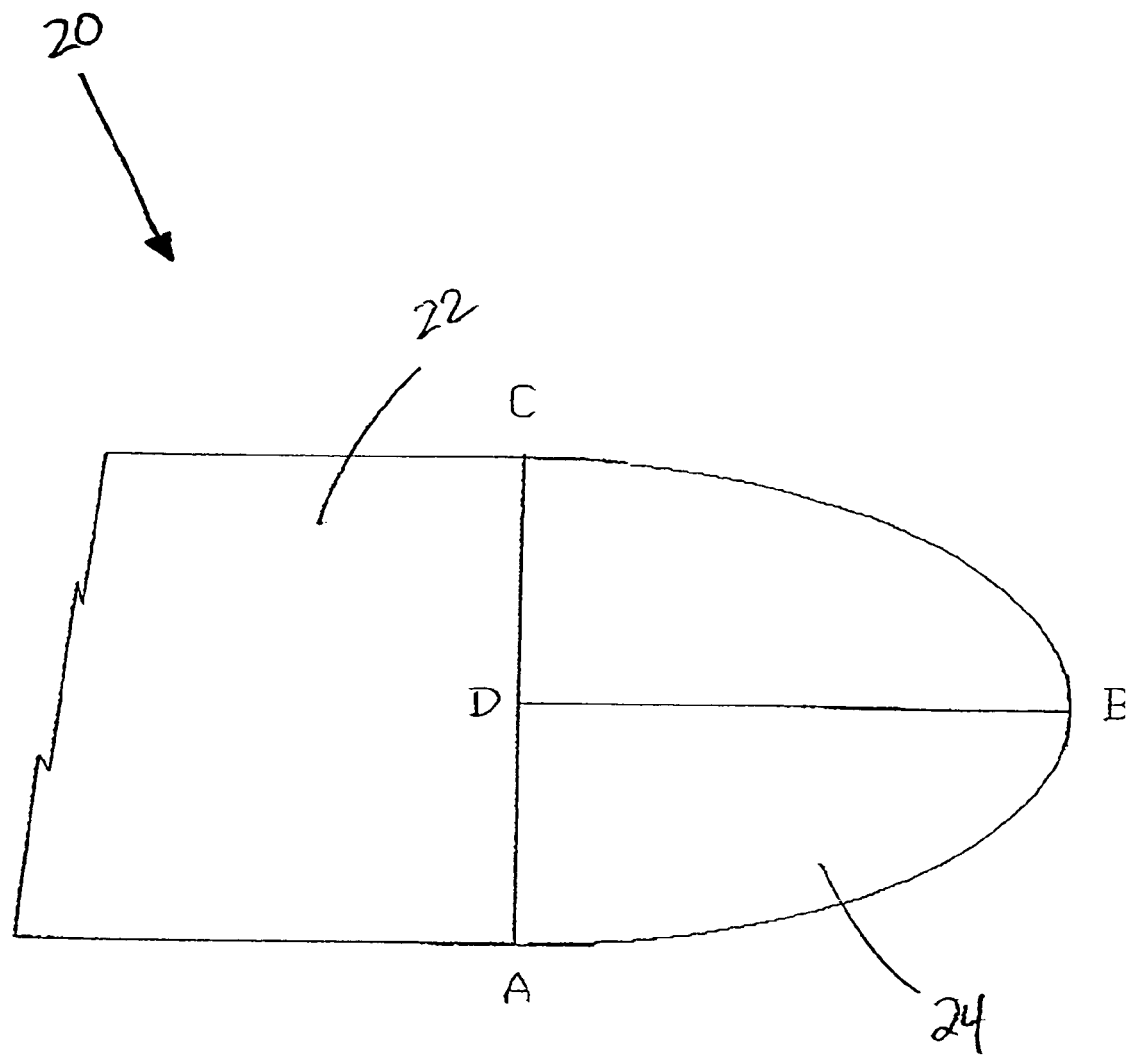
FIG. 2 is a plan view of a tapered tampon applicator insertion end according to the present invention.
Figure 3:
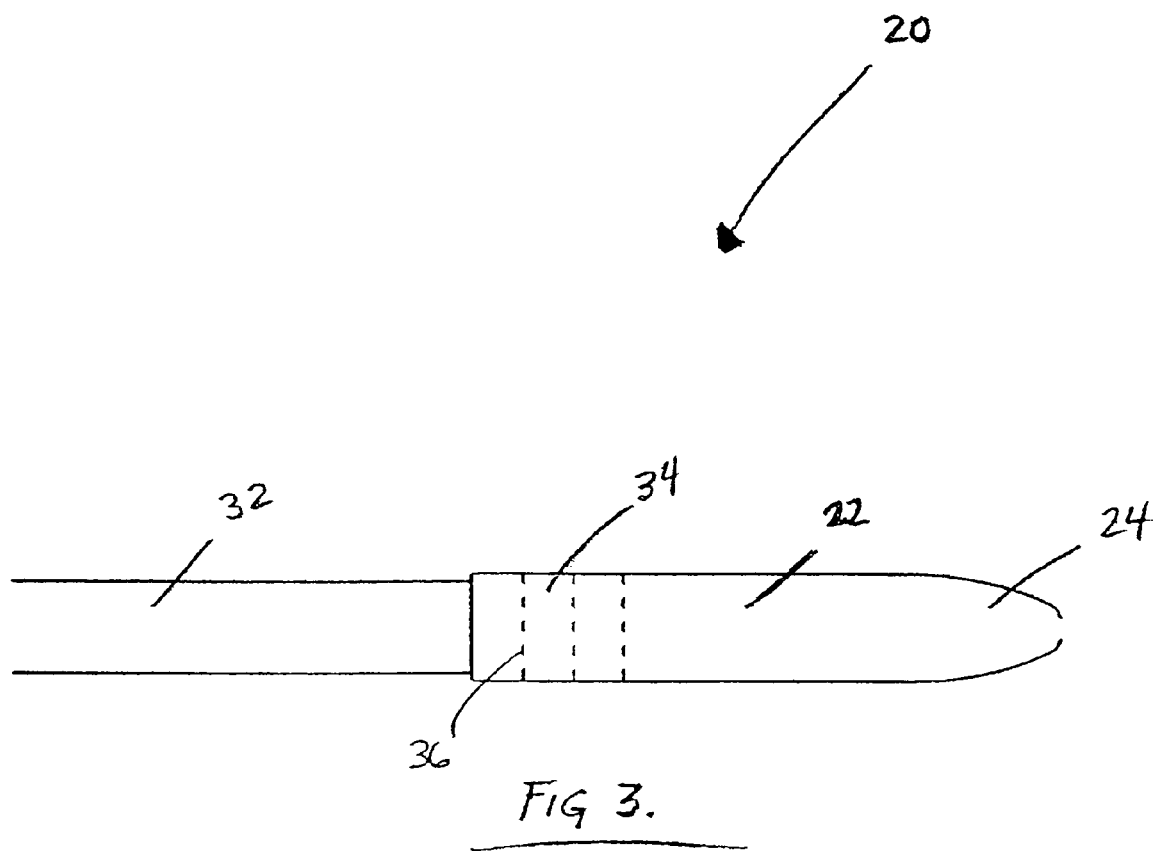
FIG. 3 is a plan view of a tapered tampon applicator according to one embodiment of the present invention.

Referring to FIGS. 2 and 3, one embodiment of the tampon applicator of the present invention is represented generally by reference numeral 20. Applicator 20 has a barrel 22 and a tapered insertion tip 24. The more gradual taper of the present invention, as opposed to the rounded or dome-shaped tip of the prior art, affords a user increased comfort, especially during insertion of applicator 20 into the vagina, by gradually parting the vulva-vaginal channel over the longer, tapered insertion tip 24. To achieve such enhanced properties, the taper ratio, represented by the ratio of the length of the taper projection along a longitudinal, centerline, or horizontal axis of the barrel BD to the projection length along a radius or vertical axis CD, is greater than 1 to about 8. Preferably, the taper ratio is about 1.35 to about 5, and more preferably about 1.4 to about 2.3. To enhance the ease of use, barrel 22 may also have a fingergrip area 34. While the shape of the line BC may be substantially straight, approximate a curve, or a combination of both, it is preferred that there is no straight section at any point along the line BC.

Through both quantitative and qualitative consumer testing, it has been determined that an applicator with a tapered tip having a ratio according to the present invention is greatly preferred to current domed-tipped applicators. Tests were performed in which an applicator with a tapered insertion tip having a ratio of approximately 1.7 and a commercial product having a domed insertion tip with a ratio of 1, as described above, were used separately. The applicator having a tapered insertion tip rated significantly higher at 95% confidence on insertion comfort and appearance of the applicator, and the belief that the applicator would make the product comfortable to use rated higher at 90% confidence. In qualitative consumer work, consumers selected the tampon of the present invention 3 to 1 over domed-tip tampon applicators because they believed the tapered insertion tips would make the applicator more comfortable to insert.

Based on this consumer data it is determined that a tapered insertion tip with a ratio in the range of the present invention provides consumer-meaningful benefits surrounding insertion comfort both in function and perception.

Figure 4:
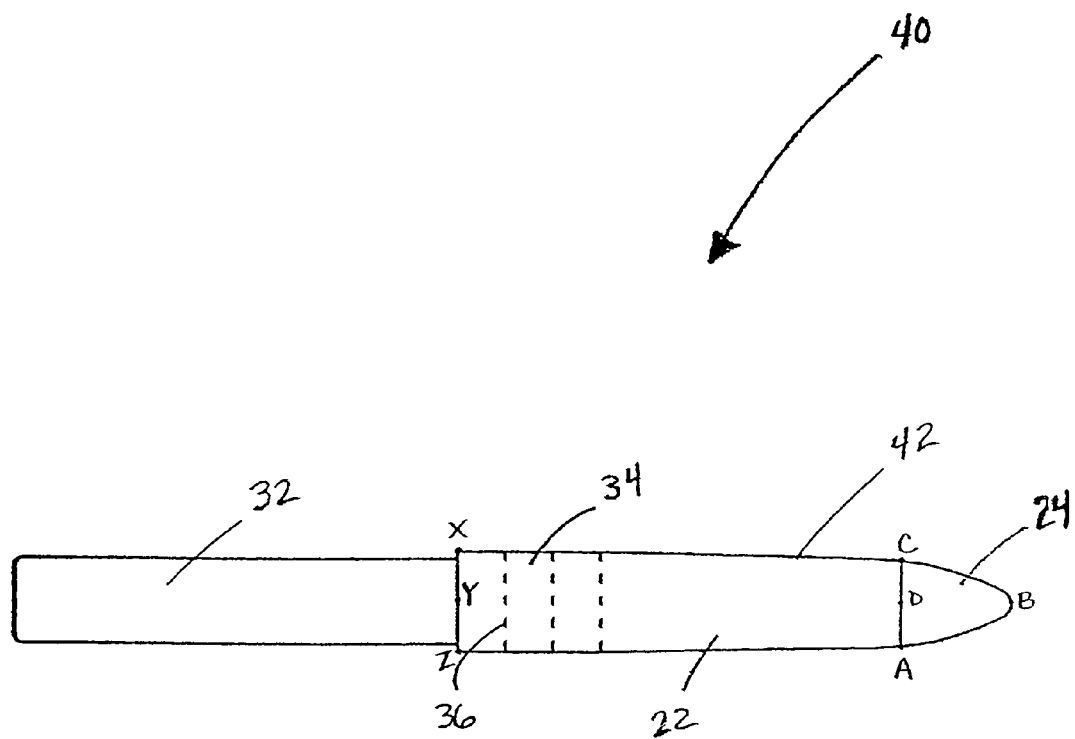
FIG. 4 is a plan view of a tapered tampon applicator according to another embodiment of the present invention.

Referring to FIG. 4, another embodiment of the tapered applicator of the present invention is represented generally by reference numeral 40. Applicator 40 has plunger 32 and barrel 22. Barrel 22 has tapered insertion tip 24, and notably tapered barrel section 42. By extending the taper from insertion tip 24 to tapered barrel section 42, user comfort is further enhanced during use by more gradually parting the vulva-vaginal channel over the increased length of tapered barrel section 42 and tapered tip 24, as opposed to just tapered insertion tip 24. To achieve this improved user comfort, the taper ratio of the barrel represented by the ratio of the largest radius XY to the radius CD of the barrel at the base of the insertion tip, is about 1.2 to about 8, and preferably about 1.25 to about 2. The taper ratio of the insertion tip represented by the ratio of the length of the taper projection along the horizontal axis of the barrel BD to the projection length along the vertical axis CD is about 1.3 to about 5, preferably about 1.4 to about 2.3, and more preferably about 1.45 to about 1.75. The angle that the tangent of surface BX at point C creates with AC may be the same or smaller than the angle that the tangent of surface BX at point X creates with XZ. The shape of curves CX and AZ may be substantially straight or they may approximate a curve, or any combinations thereof.

To enhance ease of use, barrel 22 may also have fingergrip area 34. Referring to FIGS. 3 and 4, fingergrip area 34 may be formed with any number and/or configuration of gripping structures 36, to further enhance the applicator's grippability. Fingergrip area 34 may be smooth or, more preferably, may include one or more patterned or textured structures extending above and/or below the surface of the fingergrip area.

Suitable gripping structures 36 may include, for example, one or more abrasive materials, embossments, grooves, high wet coefficient of friction materials, lances, pressure sensitive adhesives, protuberances, slits, treads, or any combinations thereof. In addition, gripping structures 36 may be formed in any shape, including, but not limited to, arc, circle, concave, cone, convex, diamond, line, pentagon, hexagon, octagon, oval, polygon, rectangle, rib, square, triangle, or any combinations thereof.

It should be understood that gripping structures 36 may be arranged circumferentially around fingergrip area 34 in any pattern suitable for forming a gripping area. For example, gripping structures 36 can form a distinct pattern, such as, rows or columns, or may be formed intermittently with breaks in structure or in any random order or pattern.

Figure 5:
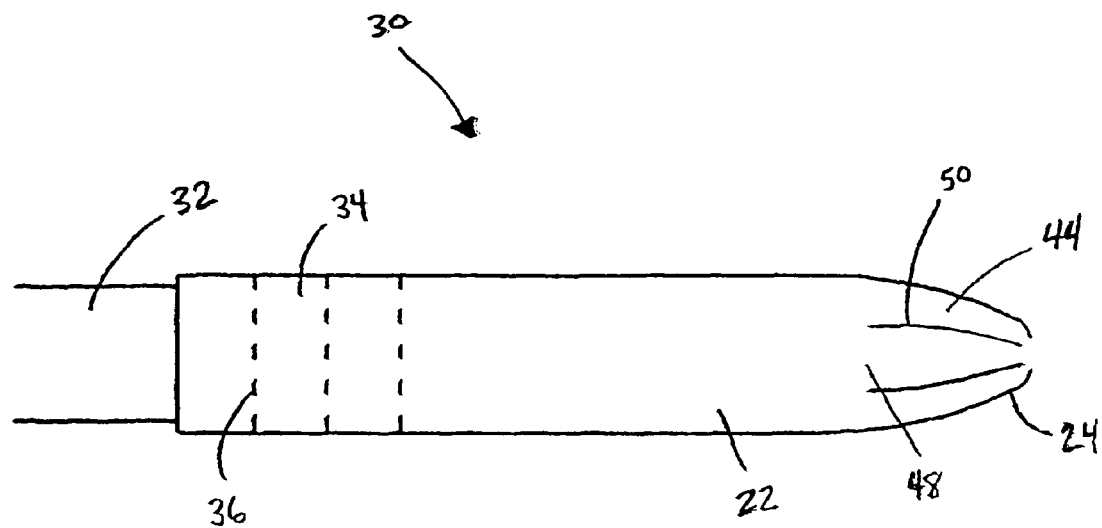
FIG. 5 is a plan view of the tapered tampon applicator of FIG. 3 with a petal-tip insertion end.
Figure 6:
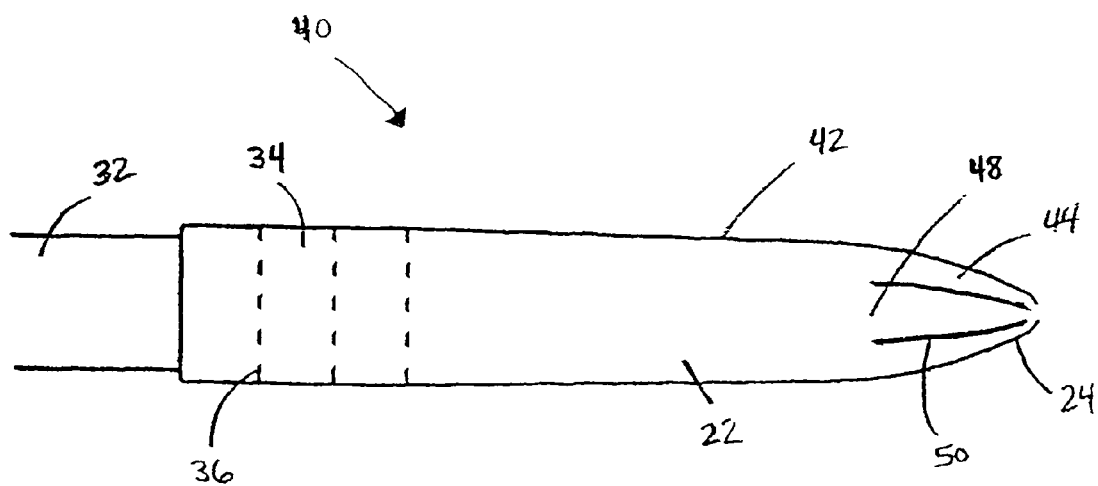
FIG. 6 is a plan view of the tapered tampon applicator of FIG. 4 with a petal-tip insertion end.

Referring to FIGS. 5 and 6, applicators 30, 40, respectively, are depicted with petals 44 formed on insertion tip 24. Insertion tip 24 has about 2 to about 12 individual petals 44, which are curved inwardly at their base region 48. Preferably, insertion tip 24 has about 2 to about 8 individual petals 44, and more preferably about 3 to about 8 individual petals. Each adjacent pair of petals 44 is separated by a radial slit 50.

Petal thickness plays an important role in two key factors of tampon performance, namely, ejection force and petal tip stability. Ejection force is the amount of force the user applies to the plunger to eject the pledget from the applicator. It is desired that this force be low to facilitate easy insertion of the pledget into the body. Petal tip stability is the tendency of the applicator petals to hold their desired shape when subjected to outside factors such as heat, moisture, and any movement that may occur during shipping and/or during insertion into the vagina. If the petal tip is unstable, the petals may "open" or collapse, releasing their desired shape, which may render the tampon uncomfortable to use or even unusable.

The thickness of the applicator petals can be altered to control and/or influence the ejection force and/or petal stability of the applicator. Thin petals, especially those below about 0.022 inches in thickness, tend to be lower in ejection force, and decreasing petal thickness may further lower ejection force. However, if the applicator material is not stiff or rigid enough, thin petals may experience tip stability problems, or may collapse inward upon insertion. In this instance, it is helpful to have a pledget whose shape closely approximates or contours to the desired shape of the tapered applicator tip, and/or is compact or dense enough to prevent the petals from collapsing.

According to the present invention, the petals on the tapered tip applicator have a petal thickness of about 0.004 inches to about 0.022 inches. Preferably, the petal thickness is about 0.008 inches to about 0.018 inches, and more preferably, about 0.009 inches to about 0.013 inches.

Increasing the petal thickness to greater than about 0.025 inches can help increase the petal stability and/or collapse issue, however this increases ejection force. If the applicator material is such that the petals have to be so thick to provide petal stability that the ejection force becomes higher than acceptable, it is contemplated that a weakened region, as discussed below, could be provided to decrease ejection force.

According to the present invention, the tapered applicator may have petals with a petal thickness of about 0.025 inches to about 0.05 inches. Preferably, the petals may have a thickness of about 0.025 inches to about 0.035 inches, and more preferably about 0.025 inches to about 0.03 inches.

If there is the balance of both ejection force and petal tip stability, there is allowed more flexibility in the pledget design. The pledget may be either rigid or amorphous, and may or may not approximate the shape of the applicator tip, as the tip may not need to be supported by the pledget.

Another important aspect of the petals is petal thickness uniformity. Petal thickness uniformity across the entire area of each petal is advantageous for several reasons. First, it can result in processing efficiencies when making the applicator. Secondly, a uniform thickness ensures that each petal will function properly both during storage and shipment of the applicator, and more importantly during use by a woman. In addition, the uniform petals may be more aesthetically pleasing to the consumer.

In accordance with the present invention, each petal is uniform or substantially uniform in thickness, in that the thickness measured at any point on a given petal does not vary more than about 25% across the entire area of the petal. Preferably, the thickness does not vary more than about 10% across the entire area of the petal. More preferably, the thickness does not vary more than about 2% across the entire area of the petal.

Figure 7:
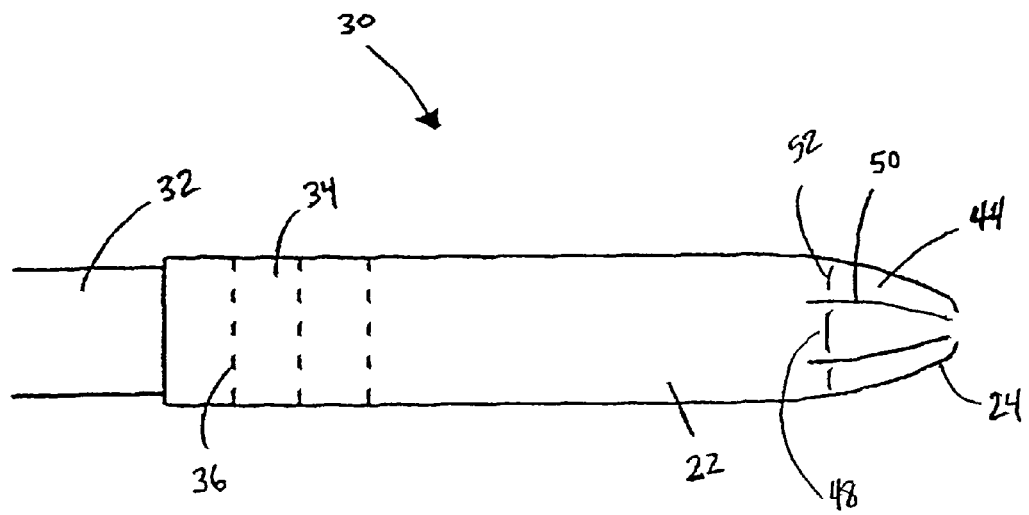
FIG. 7 is a plan view of the tapered tampon applicator of FIG. 5 with a weakened region at the base of the insertion end.

Referring to FIG. 7, in one embodiment of the present invention, one or more circumferential grooves 52 are preferably provided around the inside surface, outside surface, or both of barrel 22 at the petal base region 48 to aid in the curved inward folding of petals 44. Grooves 52 may be formed by any means known in the art. Preferably, grooves 52 are formed by scoring, etching, slitting, molding, or any combinations thereof. Grooves 52 provide a hinge point or weakened region to facilitate bending of petals 44 to their tapered configuration. In addition, the weakened region reduces the expulsion force necessary to eject an absorbent pledget from applicator 30, thus enhancing the ease of use of the applicator.

Figure 8:
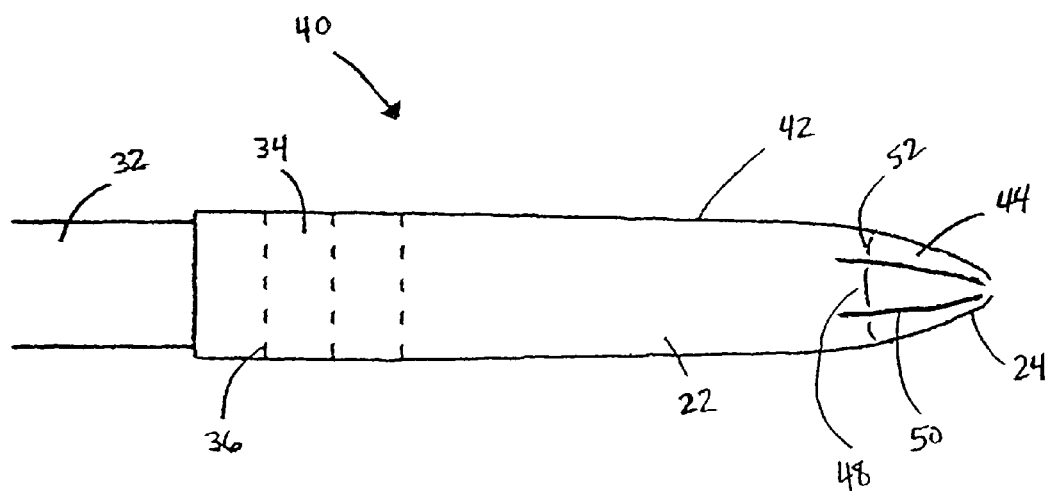
FIG. 8 is a plan view of the tapered tampon applicator of FIG. 6 with a weakened region at the base of the insertion end.

Referring to FIG. 8, in another embodiment of the present invention, radial slits 50 between the sides of each adjacent pair of petals 44 extend below base region 48, which is the area at the base of the petals, and circumferential groove 52. Advantageously, this allows for tolerances with respect to anticipated manufacturing variations in the location of grooves 52. This also reduces the expulsion force necessary to eject an absorbent pledget from applicator 40, thus enhancing the ease of use of the applicator.

In the case of any tapered tampon applicator of the present invention having a barrel with a maximum outside diameter less than 0.598 inches, the ratio of the extension of radial slits 50 beyond the centerline of the lowest set (relative to the applicator tip) of grooves 52 to the maximum barrel outside diameter is about 0.002 to about 1 and preferably about 0.167 to about 0.5. In addition, the ratio of the width of radial slits 50 at the location of the centerline at the lowest set (relative to the applicator tip) of grooves 52 to the maximum barrel outside diameter is about 0.002 to about 0.25 and preferably about 0.017 to about 0.1.

In the case of any tapered tampon applicator of the present invention having a barrel with a maximum outside diameter greater than or equal to 0.598 inches but less than 0.658 inches, the ratio of the extension of radial slits 50 beyond the centerline of the lowest set (relative to the applicator tip) of grooves 52 to the maximum outside diameter of barrel 22 is about 0.002 to about 0.669 and preferably about 0.152 to about 0.334. The ratio of the width of radial slits 50 at the location of the centerline of the lowest set (relative to the applicator tip) of grooves 52 to the maximum outside diameter of barrel 22 is about 0.002 to about 0.167 and preferably about 0.015 to about 0.067.

In the case of any tapered tampon applicator of the present invention having a barrel with a maximum outside diameter greater than or equal to 0.658 inches, the extension of radial slits 50 beyond the centerline or the lowest set (relative to the applicator tip) of grooves to the maximum outside diameter of barrel 22 is about 0.001 to about 0.608 and preferably about 0.125 to about 0.304. The width of radial slits 50 at the location of the centerline of the lowest set (relative to the applicator tip) of grooves 52 to the maximum outside diameter of barrel 22 is about 0.001 to about 0.152 and preferably about 0.013 to about 0.061.

In another embodiment of the present invention, grooves 52 may be omitted with the requisite reduction in expulsion force being obtained by the appropriate characteristics of cardboard in conjunction with the initial bending of petals 44 at their base region 48, in accordance with the invention set forth in U.S. Pat. Nos. 5,389,067 and 6,024,716 to Rejai, which are incorporated herein by reference.

Barrel 22 and/or plunger 32 of the present invention may be formed from any suitable material. Suitable materials for forming barrel 22 and/or plunger 32 include, for example, biopolymer, cardboard, cardboard laminate, heat shrink plastic, paper, paper laminate, paper slurry, plastic, plastic tubing, pulp slurry, pulp-molded paper, or any combinations thereof.

Barrel 22 and/or plunger 32 may be internally and/or externally coated with any suitable material to enhance strength and/or reduce surface friction. Suitable coatings include, for example, cellophane, cellulose, epoxy, lacquer, nitrocellulose, nylon, plastic, polyester, polylactide, polyolefin, polyvinyl alcohol, polyvinyl chloride, silicone, wax, or any combinations thereof.

Although it might be implied that the cross-sectional shape of plunger 32 and barrel 22 is circular, due to the use of the terms 'diameter' and 'radius', it should be understood that the cross-sectional shape can be non-circular, such as oval or polygonal. Furthermore, the cross-sectional shape can vary along the length of both plunger 32 and barrel 22. For example, a circular plunger with a polygonal fingergrip and an oval main body may be formed.

The foregoing specification and drawings are merely illustrative of the present invention and are not intended to limit the invention to the disclosed embodiments. Variations and changes, which are obvious to one skilled in the art are intended to be within the scope and nature of the present invention, which is defined in the appended claims.

Wherefore it is claimed:

1. A tampon applicator comprising a barrel, said barrel having a tapered insertion tip with a plurality of petals,
    wherein the insertion tip has a taper ratio greater than 1 to about 8,
    wherein the taper ratio is a length of a projection of the insertion tip taper along a longitudinal axis of the barrel to a length of a projection of the insertion tip taper along a radius of the barrel at a base region of the plurality of petals,
    wherein said plurality of petals each have a thickness of about 0.004 inches to about 0.022 inches,
    wherein said plurality of petals have a substantially uniform thickness,
    wherein said base region comprises at least one circumferential groove,
    wherein each adjacent pair of said plurality of petals is separated by a radial slit that extends below said at least one groove, and
    wherein a ratio of a width of said radial slit at said groove to a maximum outside diameter of said barrel is about 0.002 to about 0.25.

2. The applicator of claim 1, wherein said taper ratio is about 1.3 to about 5.

3. The applicator of claim 1, wherein said taper ratio is about 1.4 to about 2.3.

4. The applicator of claim 1, wherein said taper ratio is about 1.45 to about 1.75.

5. The applicator of claim 1, wherein said plurality of petals each have a thickness of about 0.008 inches to about 0.018 inches.

6. The applicator of claim 1, wherein said plurality of petals each have a thickness of about 0.009 inches to about 0.013 inches.

7. The applicator of claim 1, wherein said substantially uniform thickness of each of said plurality of petals varies no more than about 25% across an entire area of said petals.

8. The applicator of claim 1, wherein said substantially uniform thickness of each of said plurality of petals varies no more than about 10% across an entire area of said petals.

9. The applicator of claim 1, wherein said substantially uniform thickness of each of said plurality of petals varies no more than about 2% across an entire area of said petals.

10. The applicator of claim 1, wherein said barrel has a barrel taper ratio represented by a ratio of a largest radius of the barrel to a radius of the barrel at a base of the insertion tip of about 1.2 to about 8.

11. The applicator of claim 10, wherein said barrel taper ratio is about 1.25 to about 2.

12. The applicator of claim 1, wherein said barrel has a fingergrip.

13. The applicator of claim 12, wherein said fingergrip has at least one gripping structure.

14. The applicator of claim 13, wherein said at least one gripping structure is circumferentially disposed around said fingergrip.

15. The applicator of claim 13, wherein said at least one gripping structure is selected from the group consisting of one or more abrasive materials, embossments, grooves, high wet coefficient of friction materials, lances, pressure sensitive adhesives, protuberances, slits, treads, and any combinations thereof.

16. The applicator of claim 13, wherein said at least one gripping structure is formed in a shape selected from the group consisting of arc, circle, concave, cone, convex, diamond, hexagon, line, octagon, oval, pentagon, polygon, rectangle, rib, square, triangle, and any combinations thereof.

17. The applicator of claim 13, wherein said at least one gripping structure is raised, depressed, or a combination thereof.

18. The applicator of claim 1, wherein said plurality of petals is about two petals to about eight petals.

19. The applicator of claim 1, wherein said maximum outside diameter less than 0.598 inches.

20. The applicator of claim 19, further comprising a ratio of an extension of said radial slit beyond said groove, relative to the applicator tip, to said maximum outside diameter of said barrel of about 0.002 to about 1.

21. The applicator of claim 1, wherein said maximum outside diameter of greater than or equal to 0.598 inches to less than 0.658 inches.

22. The applicator of claim 21, further comprising a ratio of an extension of said radial slit beyond said groove, relative to the applicator tip, to said maximum outside diameter of said barrel of about 0.002 to about 0.669.

23. The applicator of claim 21, wherein said ratio of said width of said radial slit at said groove to said maximum outside diameter of said barrel of about 0.002 to about 0.167.

24. The applicator of claim 1, wherein said maximum outside diameter greater than or equal to 0.658 inches.

25. The applicator of claim 24, further comprising a ratio of an extension of said radial slit beyond said groove, relative to the applicator tip, to said maximum outside diameter of said barrel of about 0.001 to about 0.608.

26. The applicator of claim 24, wherein said ratio of said width of said radial slit at said groove to said maximum outside diameter of said barrel of about 0.001 to about 0.152.

27. The applicator of claim 18, wherein said about 2 to about 8 petals have a weakened base region formed by bending said petals back and forth, thereby breaking one or more bonds.

28. The applicator of claim 1, wherein said barrel is formed from a material selected from the group consisting of biopolymer, cardboard, cardboard laminate, heat shrink plastic, paper, paper slurry, paper laminate, plastic, plastic tubing, pulp slurry, pulp-molded paper, and any combinations thereof.

29. The applicator of claim 1, wherein said barrel is formed from cardboard.

30. The applicator of claim 1, wherein said barrel has a surface that is coated with a material selected from the group consisting of cellophane, cellulose, epoxy, lacquer, nitrocellulose, nylon, plastic, polyester, polylactide, polyolefin, polyvinyl alcohol, polyvinyl chloride, silicone, wax, and any combinations thereof.

31. The applicator of claim 30, wherein said surface is selected from the group consisting of an outer surface, an inner surface, and any combination thereof.

32. A tampon applicator comprising:
a barrel with a tapered insertion tip,
wherein said tapered insertion tip has a taper ratio represented by a ratio of a length of a projection of the insertion tip taper along a longitudinal axis of the barrel to a length of a projection of the insertion tip taper along a radius of the barrel at a base region of one or more petals of greater than 1 to about 8,
wherein said barrel is formed from a material selected from the group consisting of cardboard, cardboard laminate, paper, paper laminate, pulp slurry, paper slurry, biopolymer, pulp-molded paper, and any combinations thereof,
wherein said base region comprises at least one circumferential groove,
wherein the barrel comprises a longitudinally extending radial slit that traverses said at least one groove, and
wherein a ratio of a width of said radial slit at said groove to a maximum outside diameter of said barrel is about 0.002 to about 0.25.

33. The applicator of claim 32, wherein said taper ratio is about 1.5 to about 5.

34. The applicator of claim 32, wherein said taper ratio is about 1.4 to about 2.3.

35. The applicator of claim 32, wherein said taper ratio is about 1.45 to about 1.75.

36. The applicator of claim 32, wherein said one or more petals each have a thickness of about 0.008 inches to about 0.018 inches.

37. The applicator of claim 32, wherein said one or more petals each have a thickness of about 0.009 inches to about 0.013 inches.

38. The applicator of claim 32, wherein said one or more petals have a substantially uniform thickness.

39. The applicator of claim 38, wherein said substantially uniform thickness of each of said one or more petals varies no more than about 25% across an entire area of said one or more petals.

40. The applicator of claim 38, wherein said substantially uniform thickness of each of said one or more petals varies no more than about 10% across an entire area of said one or more petals.

41. The applicator of claim 38, wherein said substantially uniform thickness of each of said one or more petals varies no more than about 2% across an entire area of said one or more petals.

42. The applicator of claim 32, wherein said barrel has a barrel taper ratio represented by a ratio of a largest radius of the barrel to a radius of the barrel at a base of the insertion tip of about 1.2 to about 8.

43. The applicator of claim 42, wherein said barrel taper ratio is about 1.25 to about 2.

44. The applicator of claim 32, wherein said barrel has a fingergrip.

45. The applicator of claim 44, wherein said fingergrip has at least one gripping structure.

46. The applicator of claim 45, wherein said at least one gripping structure is circumferentially disposed around said fingergrip.

47. The applicator of claim 45, wherein said at least one gripping structure is selected from the group consisting of one or more abrasive materials, embossments, grooves, high wet coefficient of friction materials, lances, pressure sensitive adhesives, protuberances, slits, treads, and any combinations thereof.

48. The applicator of claim 45, wherein said at least one gripping structure is formed in a shape selected from the group consisting of arc, circle, concave, cone, convex, diamond, hexagon, line, octagon, oval, pentagon, polygon, rectangle, rib, square, triangle, and any combinations thereof.

49. The applicator of claim 45, wherein said at least one gripping structure is raised, depressed, or a combination thereof.

50. The applicator of claim 32, wherein said one or more petals is about two to about eight petals.

51. The applicator of claim 50, wherein an adjacent pair of said about two to about eight petals is separated by said radial slit.

52. The applicator of claim 32, wherein said maximum outside diameter less than 0.598 inches.

53. The applicator of claim 52, further comprising a ratio of an extension of said radial slit beyond said groove, relative to the applicator tip, to said maximum outside diameter of said barrel of about 0.002 to about 1.

54. The applicator of claim 32, wherein said maximum outside diameter of greater than or equal to 0.598 inches to less than 0.658 inches.

55. The applicator of claim 54, further comprising a ratio of an extension of said radial slit beyond said groove, relative to the applicator tip, to said maximum outside diameter of said barrel of about 0.002 to about 0.669.

56. The applicator of claim 54, wherein said ratio of said width of said radial slit at said groove to said maximum outside diameter of said barrel of about 0.002 to about 0.167.

57. The applicator of claim 32, wherein said maximum outside diameter greater than or equal to 0.658 inches.

58. The applicator of claim 57, further comprising a ratio of an extension of said radial slit beyond said groove, relative to the applicator tip, to said maximum outside diameter of said barrel of about 0.001 to about 0.608.

59. The applicator of claim 57, wherein said ratio of said width of said radial slit at said groove to said maximum outside diameter of said barrel of about 0.001 to about 0.152.

60. The applicator of claim 32, wherein said one or more petals have a weakened base region formed by bending said petals back and forth, thereby breaking one or more bonds.

61. The applicator of claim 32, wherein said barrel is formed from cardboard.

62. The applicator of claim 32, wherein said barrel has a surface that is coated with a material selected from the group consisting of cellophane, cellulose, epoxy, lacquer, nitrocellulose, nylon, plastic, polyester, polylactide, polyolefin, polyvinyl alcohol, polyvinyl chloride, silicone, wax, and any combinations thereof.

63. The applicator of claim 62, wherein said surface is selected from the group consisting of an outer surface, an inner surface, and any combination thereof.

64. A tampon applicator comprising a tapered barrel and an insertion tip, wherein said tapered barrel has a taper ratio of about 1.2 to about 8,
  wherein the taper ratio is a ratio of a largest radius of said tapered barrel to a radius of said tapered barrel at a base region of said insertion tip,
  wherein said base region comprises a circumferential groove,
  wherein said insertion comprises a plurality of petals, each pair of adjacent petals being separated by a longitudinally extending radial slit that traverses said groove,
  wherein a ratio of a width of said radial slit at said groove to a maximum outside diameter of said barrel is about 0.002 to about 0.25.

65. The applicator of claim 64, wherein said taper ratio is about 1.25 to about 2.

* * * * *